United States Patent [19]

Exner et al.

[11] Patent Number: 5,696,170
[45] Date of Patent: Dec. 9, 1997

[54] CHEMICAL DISINFECTANT BASED ON PHENOLIC ACTIVE COMPONENTS AND GLUTARALDEHYDE

[75] Inventors: Otto Exner, Ratingen; Manfred Hoffmann, Tönisvorst, both of Germany

[73] Assignee: Bayer Aktiengesellschaft, Leverkusen, Germany

[21] Appl. No.: 553,483

[22] PCT Filed: May 16, 1994

[86] PCT No.: PCT/EP94/01572

§ 371 Date: Nov. 21, 1995

§ 102(e) Date: Nov. 21, 1995

[87] PCT Pub. No.: WO94/27437

PCT Pub. Date: Dec. 8, 1994

[30] Foreign Application Priority Data

May 28, 1993 [DE] Germany ............. 43 17 844.8

[51] Int. Cl.[6] .................. A01N 35/00; A01N 31/08

[52] U.S. Cl. .................. 514/693; 514/736; 514/737
[58] Field of Search .................. 514/737, 693, 514/736

[56] References Cited

U.S. PATENT DOCUMENTS

| 3,917,850 | 11/1975 | Boucher | 424/333 |
| 4,654,374 | 3/1987 | Martin | 514/698 |
| 5,250,573 | 10/1993 | Magni | 514/701 |

OTHER PUBLICATIONS

Martindale, The Extra Pharmacopoeia, 28th edition, pp. 564–565, 558 and 1290, 1982.

*Primary Examiner*—Raymond Henley, III
*Attorney, Agent, or Firm*—Sprung Horn Kramer & Woods

[57] ABSTRACT

Described is the use of microbicidal phenolic compounds in combination with glutaraldehyde for the preparation of disinfectants which are suitable for the disinfection of surfaces and instruments, but also of parts of the body, in hospitals and doctors' surgeries.

5 Claims, No Drawings

CHEMICAL DISINFECTANT BASED ON PHENOLIC ACTIVE COMPONENTS AND GLUTARALDEHYDE

The invention relates to the use of microbicidal phenolic compounds in combination with glutaraldehyde for the preparation of disinfectants which are suitable for the disinfection of surfaces and instruments, but also of parts of the body (for example hands) in hospitals and doctors' surgeries.

It is known that there is a considerable risk of infection for patients and staff in hospitals and in doctors' surgeries from microorganisms such as bacteria, yeasts and viruses which are pathogenic to humans. Taking into account this risk of infection for patients and staff, the disinfection of surfaces and instruments in hospitals and doctors' surgeries is of particular importance. Apart from the known causative agents of hospitalism from amongst the bacteria and yeasts, viruses have gained increasing importance amongst disinfection procedures.

The requirements regarding the effectiveness of disinfectants are described, for example, in the regulations of the DGHM (Dt. Gesellschaft für Hygiene und Mikrobiologie [German Society for Hygiene and Microbiology]) and the guideline of the Bundesgesundheitamt (BGA [Federal Health Office]) and the Dt. Vereinigung zur Bekämpfung von Viruserkrankungen (DVV [German Association for Vital Disease Research]). Disinfectants which meet the DGHM requirements are listed in the VII list as per 1.1.92. Nothing is mentioned as yet in these lists on the virucidal properties of the disinfectants.

When used at concentrations, and over periods, which are relevant under realistic conditions, the combination according to the invention guarantees a greatly reduced number of pathogenic microorganisms amongst bacteria and yeasts and also inactivation of, for example, DVV-listed, naked and enveloped viruses while fully meeting current requirements. The invention is based on a combination of microbicidal phenolic compounds (ph) and glutaraldehyde (glu).

Phenolic active substances for the disinfection of surfaces and instruments are known (Ullmann-Enzyklopädie der tech. Chemie [Ullmann's Encyclopaedia of Chemical Engineering], 4th Edition, 1975, Volume 20, pp. 41–58). It is furthermore known that microbicidal phenolic compounds have an insufficient activity against naked viruses. It is also known that inactivation of naked viruses, such as polio, is made possible by concentration from 1% of glutaraldehyde (10,000 ppm) in alkaline solution.

CA 2.015.079 describes a disinfectant composed of glu, o-phenylphenol, p-tert-amylphenol, sodium arylalkylsulphonate, citric acid and water. A combination of the abovementioned active substances allows stabilization and an activity specifically against bacteria which are pathogenic to humans, even in the acidic range. A virucidal activity is not described. Moreover, this formulation comprises an extremely large amount of glu, which results in odour and corrosion problems and might, under certain circumstances, cause allergic reactions.

The invention therefore relates to the use of a combination of glutaraldehyde and 2-phenyl-phenol and/or para-chloro-meta-cresol for the disinfection of surfaces, instruments and parts of the body.

The combinations according to the invention meet the following requirements as disinfectants:

broad activity against bacteria (yeasts) and viruses which are pathogenic to humans;

within a realistic timespan, the numbers of microorganisms or viruses which exist on the surfaces are reduced reliably to a level that meets requirements:

the active substance components employed were chosen in such a way that optimal effectiveness is achieved using the lowest possible use concentrations, both of phenolic microbicides and of glu;

very low concentrations of glu in the use solutions minimize the hazard potential of odour nuisance, of a potential sensitization and of discolouring (of the skin) while maintaining full virucidal effectiveness;

use of readily biodegradable surfactants which are kind to the skin;

the shelf life of the disinfectant concentrates is not less than a year.

The combinations according to the invention are generally in the form of liquid concentrated formulations which are generally used according to the invention after dilution with water.

In general, the concentrates according to the invention comprise 2–20% by weight, preferably 3–15% by weight, and especially 3–12% by weight, of the microbocidal phenolic compounds. If appropriate, the ratio between o-phenylphenol and para-chloro-meta-cresol is 100:0 to 0:100 parts by weight.

Moreover, the concentrates according to the invention comprise 2–50% by weight, preferably 2–10% by weight and especially 2–5% by weight, of glutaraldehyde.

Moreover, the concentrates according to the invention preferably comprise acidifiers, such as citric acid, lactic acid and malic acid to bring the pH of the preparations to 2 to 7, preferably 2.3 to 5, especially 2.5 to 4.

The concentrates according to the invention furthermore preferably comprise up to 50% by weight, in particular 10 to 40% by weight, of auxiliaries, such as surfactants, preferably anionic, optionally ethoxylated surfactants, such as, for example, secondary alkylsulphonates having 12 to 14 carbon atoms on average, alkylsulphosuccinates and/or alkyl ether sulphonates, diluents such as, for example, alcohols, preferably isopropanol, 1,2-propanediol, glycols and/or diluents which are miscible with water, and customary auxiliaries such as perfumes, corrosion inhibitors such as benzotriazole or tolyltriazole, colourants and/or complexing agents and, if appropriate, other substances which act as disinfectants.

The concentrates according to the invention furthermore comprise up to 75% by weight, in particular 10 to 50% by weight, of water.

A preferred concentrate comprises

5–15% by weight of phenolic compounds
3–4% by weight of glutaraledehyde
10–20% by weight of organic diluents
5–25% by weight of surfactants
and water up to 100% by weight.

The preparations according to the invention are commercially available as concentrates and are generally used in the form of aqueous dilutions. The aqueous dilutions preferably comprise 0.5 to 5% of the combinations according to the invention.

The preparations according to the invention are prepared in the customary manner by adding the individual components and mixing thoroughly until clear solutions are obtained.

EXAMPLES

To test the disinfectant combination according to the invention for its microbicidal and virucidal activity, a concentrate of the following composition is prepared by mixing the individual components.

| | Example 1 | Example 2 | Example 3 | Example 4 |
|---|---|---|---|---|
| | 4.5% by weight of para-chloro-meta-cresol | — | 11.5% by weight of PCMC | 4.8% by weight of PCMC |
| | 7.0% by weight of ortho-phenylphenol | 11.5% by weight of OPP | — | 4.8% by weight of pine oil |
| | 3.75% by weight of glutaraldehyde | 11.5% by weight of OPP | " | 4.8% by weight of pine oil |
| | 2.0% by weight of lactic acid | 11.5% by weight of OPP | " | 4.8% by weight of pine oil |
| | 15.0% by weight of isopropanol | 11.5% by weight of OPP | " | 4.8% by weight of pine oil |
| | 10.0% by weight of diisooctyl sulfosuccinate | 11.5% by weight of OPP | " | 4.8% by weight of pine oil |
| | 10.0% by weight of sodium lauryl ether sulfate (2 EO) made up to 100% with demineralized water | 11.5% by weight of OPP | " | 4.8% by weight of pine oil |

Testing for Bacteriological Activity

A. Qualitative suspension disinfection in accordance with the Guidelines for Testing and Assessing Chemical Disinfectant Methods/DGHM (as per 01.01.81) (Deutsche Gesellschaft für Hygiene und Mikrobiologie, Stuttgart-New York; Fischer Section 1 (J. Borneff; Special Edition 1.1.1981)).

100% of the microorganisms indicated in Table 1 are destroyed after a contact period of 5 minutes by the following dilutions of the concentrate of Example 1.

TABLE 1

| Test microorganisms | | Use concentration in % contact period of 5 minutes |
|---|---|---|
| *Staphyococcus aureus* | ATCC 6538 | 0.75 |
| *Escherichia coli* | ATCC 11229 | 0.50 |
| *Proteus mirabilis* | ATCC 14153 | 0.50 |
| *Pseudomonas aeruginosa* | ATCC 15442 | 0.50 |
| *Candida albicans* | ATCC 10231 | 0.25 |
| *Aspergillus flumigatus* | DSM 819 | 1.00 |

B. Tuberculocidal activity, test with carriers of microorganisms modified in accordance with DGHM Guideline I/2.4.2 (Test report; L & S GmbH Bad Bocklet, Leimbeck/Gr ötsch 8.1.1993)

TABLE 2

After the exposure times indicated, a tuberculocidal activity was found with the following use concentrations in %:

| | Exposure time in minutes | | | |
|---|---|---|---|---|
| Test organism | 15 | 30 | 60 | 120 |
| *Mycobakterium terrae* ATCC 15755 | 3 | 2 | 2 | 2 % |

Virucidal Efficacy Data

C. Virucidal effectiveness against Hepatitis B (HBV) and HIV in accordance with "DNS polymerase test" and HIV after the "Richtlinie des Bundesgesundheitsamt und der Deutschen Vereinigung zur Bekämpfung der Viruskrankheiten zur Prüfung von chemischen Desinfektionsmitteln auf Wirksamkeit gegen Viren" [Guideline of the Federal Health Office and the German Association for Virus Disease Research for Testing chemical Disinfectants for antiviral activity]. (Test report; Steinmann 28.1.1993, Staatl. Hygieneinstitut Bremen)

The following use concentrations in % and the following exposure times are determined.

| Virus | % | Exposure time in minutes |
|---|---|---|
| Hepatitis B | 1.0 | 30 |
| | 0.5 | 60 |
| HIV-1 | 1.0 | 30 |
| | 0.5 | 60 |

D. Virucidal activity against viruses as stipulated by the DVV in accordance with "Richtlinie des Bundesgesundheitsamt (BGA) und der Deutschen Vereinigung zur Bekämpfung der Viruskrankheiten (DVV) zur Bekämpfung von chemischen Desinfektionsmitteln auf Wirksamkeit gegen Viren" [Guideline of the Federal Health Office and the German Association for Vital Disease Research for the control of chemical Disinfectants for antiviral Activity]. (Test report; Steinmann 28.1.1993, Staatl. Hygieneinstitut Bremen)

The following use concentrations in % are required for inactivating the important viruses given below:

| Virus | % | Exposure time in minutes |
|---|---|---|
| Papovavirus SV 40 | 3.0 | 60 |
| Herpes simplex virus (HSV) type 1 | 0.5 | 5 |
| Polio virus type 1 strain Malhony/Pette | 4.0 | 5 |
| Vacciniavirus strain Elstree | 0.5 | 5 |
| Adenovirus type 2 strain adenoid | 1.0 | 30 |

We claim:

1. A method of disinfecting an area against microbial attack wherein the microbes include naked viruses which comprises administrating in said area a microbially effective amount of a composition comprising (a) at least one of 2-phenyl-phenol and para-chloro-meta cresol, and (b) glutaraldehyde, the glutaraldehyde being present in lesser amount than (a).

2. A method according to claim 1, wherein said composition further includes an acidifier.

3. A method according to claim 1, wherein the composition is in the form of a concentrated aqueous solution, the concentration of (a) ranging from about 5–15% by weight, and that of (b) from about 3–4% by weight and wherein the concentrated solution is diluted to 0.5–5% to provide a concentration of (a) of from 0.025–0.75% and a concentration of (b) of from 0.015–0.2%.

4. A method according to claim 1, wherein the composition is in the form of a concentrated aqueous solution, the concentration of (a) being about 11.5% by weight, and that of (b) being about 3.75% by weight and wherein the concentrated solution is diluted to 0.5–5% to provide a concentration of (a) of from 0.0575–0.575% and a concentration of (b) of from 0.01875–0.1875%.

5. A method according to claim 4, wherein the composition further includes lactic acid as an acidifier.

* * * * *